United States Patent
Kandula

(10) Patent No.: US 10,933,052 B2
(45) Date of Patent: *Mar. 2, 2021

(54) COMPOSITIONS AND METHODS FOR THE TREATMENT OF EYE DISORDERS

(71) Applicant: Cellix Bio Private Limited, Hyderabad (IN)

(72) Inventor: Mahesh Kandula, Andhra Pradesh (IN)

(73) Assignee: Cellix Bio Private Limited, Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/790,492

(22) Filed: Feb. 13, 2020

(65) Prior Publication Data
US 2020/0179343 A1  Jun. 11, 2020

Related U.S. Application Data

(63) Continuation of application No. PCT/IB2018/057342, filed on Sep. 22, 2018.

(30) Foreign Application Priority Data

Nov. 17, 2017 (IN) .............................. 201741041231

(51) Int. Cl.
A61K 31/4178 (2006.01)
A61K 31/385 (2006.01)
A61K 9/00 (2006.01)
A61P 27/06 (2006.01)

(52) U.S. Cl.
CPC ........ *A61K 31/4178* (2013.01); *A61K 9/0048* (2013.01); *A61K 31/385* (2013.01); *A61P 27/06* (2018.01)

(58) Field of Classification Search
CPC .............. A61K 31/4178; A61K 9/0048; A61K 31/385; A61P 27/06
USPC ....................................................... 514/385
See application file for complete search history.

(56) References Cited

U.S. PATENT DOCUMENTS

| | | |
|---|---|---|
| 4,835,174 A | 5/1989 | Amstutz et al. |
| 4,977,176 A | 12/1990 | Amstutz et al. |
| 5,322,942 A | 6/1994 | Rapoport et al. |
| 5,444,082 A | 8/1995 | Frigerio et al. |
| 5,530,136 A | 6/1996 | Reimann |
| 5,585,397 A | 12/1996 | Tung et al. |
| 5,723,490 A | 3/1998 | Tung |
| 5,783,701 A | 7/1998 | Tung et al. |
| 5,811,428 A | 9/1998 | Suto et al. |
| 5,994,378 A | 11/1999 | Matsuo et al. |
| 6,222,039 B1 | 4/2001 | Scalone et al. |
| 6,277,997 B1 | 8/2001 | Scalone et al. |
| 7,098,209 B2 | 8/2006 | Orme |
| 7,456,200 B2 | 11/2008 | Arora et al. |
| 7,601,840 B2 | 10/2009 | Moon et al. |
| 7,659,279 B2 | 2/2010 | Hennequin et al. |
| 7,767,689 B2 | 8/2010 | Moon et al. |
| 7,951,804 B2 | 5/2011 | Cezanne et al. |
| 7,989,458 B2 | 8/2011 | Leblanc et al. |
| 8,076,352 B2 | 12/2011 | Cao |
| 8,076,353 B2 | 12/2011 | Cao |
| 8,367,694 B2 | 2/2013 | Moon |
| 8,372,860 B2 | 2/2013 | Moon et al. |
| 8,431,578 B2 | 4/2013 | Hunt |
| 8,673,970 B2 | 3/2014 | Eissenstat et al. |
| 8,957,065 B2 | 2/2015 | Cha |
| 9,012,498 B2 | 4/2015 | Manoharan |

(Continued)

FOREIGN PATENT DOCUMENTS

| | | |
|---|---|---|
| CN | 104387364 | 3/2015 |
| DE | 2636559 | 3/1977 |

(Continued)

OTHER PUBLICATIONS

Li et al., A potential carrier based on liquid crystal nanoparticles for ophthalmic delivery of pilocarpine nitrate, 2013, International Journal of Pharmaceutics, 455, 75-84 (Year: 2013).*

(Continued)

*Primary Examiner* — Kristin A Vajda
(74) *Attorney, Agent, or Firm* — S. Elizabeth Miller, Esq.

(57) ABSTRACT

Aspects of the present disclosure provide compound of Formula I and pharmaceutically acceptable hydrates, solvates, crystals, co-crystals, enantiomers, stereoisomers, polymorphs and prodrugs thereof that can find utility in treatment of eye disorders and complications associated therewith. Aspects of the present disclosure also relate to methods of treating an eye disorder and/or complications thereof in a subject in need thereof by administering the compound of Formula I or a pharmaceutically acceptable hydrate, solvate, crystal, enantiomer, stereoisomer, polymorph or prodrug thereof.

Formula I

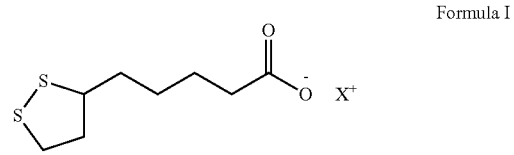

wherein, $X^+$ represents,

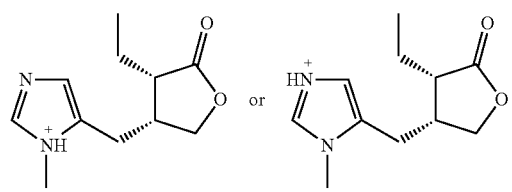

22 Claims, No Drawings

(56) References Cited

U.S. PATENT DOCUMENTS

| | | |
|---|---|---|
| 9,096,548 B2 | 8/2015 | Wiedenmayer |
| 9,173,886 B2 | 11/2015 | Guenther |
| 9,345,719 B2 | 5/2016 | Cha et al. |
| 9,365,520 B2 | 6/2016 | Yamamoto et al. |
| 9,376,436 B2 | 6/2016 | Witty et al. |
| 9,388,140 B2 | 7/2016 | Klar et al. |
| 9,458,156 B2 | 10/2016 | Norris et al. |
| 9,493,444 B2 | 11/2016 | Schiemann et al. |
| 9,549,963 B2 | 1/2017 | Liu et al. |
| 9,630,924 B2 | 4/2017 | Yamamoto et al. |
| 9,682,922 B2 | 6/2017 | Manoharan et al. |
| 9,751,879 B2 | 9/2017 | Norris et al. |
| 2002/0156076 A1 | 10/2002 | Chow et al. |
| 2003/0228299 A1 | 12/2003 | Droy-Lefaix |
| 2004/0152699 A1 | 8/2004 | Arora et al. |
| 2005/0282849 A1 | 12/2005 | Moon et al. |
| 2009/0156606 A1 | 6/2009 | Sharma |
| 2009/0326004 A1 | 12/2009 | Kumar et al. |
| 2010/0168093 A1 | 7/2010 | Pericas-Brondo |
| 2011/0091459 A1 | 4/2011 | Gant et al. |
| 2011/0124626 A1 | 5/2011 | Pooni et al. |
| 2012/0129841 A1 | 5/2012 | Cao |
| 2014/0221467 A1 | 8/2014 | Mylari |
| 2014/0228384 A1 | 8/2014 | Bustos et al. |
| 2014/0255392 A1 | 9/2014 | Koppitz et al. |
| 2016/0129006 A1 | 5/2016 | Guenther et al. |
| 2016/0229868 A1 | 8/2016 | Cha et al. |
| 2016/0303134 A1 | 10/2016 | Liu et al. |
| 2020/0040003 A1* | 2/2020 | Kandula ............... C07C 271/12 |

FOREIGN PATENT DOCUMENTS

| | | |
|---|---|---|
| DE | 2644250 | 4/1977 |
| EP | 404175 | 12/1990 |
| EP | 2130830 | 12/2009 |
| FR | 2424930 | 11/1979 |
| JP | 2012230356 | 11/2012 |
| WO | 9221675 | 12/1992 |
| WO | 9633184 | 10/1996 |
| WO | 9709315 | 3/1997 |
| WO | 9727190 | 7/1997 |
| WO | 2001000586 | 1/2001 |
| WO | 2002098877 | 12/2002 |
| WO | 2004026258 | 4/2004 |
| WO | 2004096226 | 11/2004 |
| WO | 2005056528 | 6/2005 |
| WO | 2007128460 | 11/2007 |
| WO | 2008006583 | 1/2008 |
| WO | 2008127715 | 10/2008 |
| WO | 2009087224 | 7/2009 |
| WO | 2009105782 | 8/2009 |
| WO | 2010007382 | 1/2010 |
| WO | 2011113060 | 9/2011 |
| WO | 2011135303 | 11/2011 |
| WO | 2011162515 | 12/2011 |
| WO | 2012041158 | 4/2012 |
| WO | 2012065057 | 5/2012 |
| WO | 2012075046 | 6/2012 |
| WO | 2012079032 | 6/2012 |
| WO | 2012130905 | 10/2012 |
| WO | 2012136531 | 10/2012 |
| WO | 2013027001 | 2/2013 |
| WO | 2013093497 | 6/2013 |
| WO | 2013144191 | 10/2013 |
| WO | 2014104784 | 7/2014 |
| WO | 2015018754 | 2/2015 |
| WO | 2015082378 | 6/2015 |
| WO | 2015082376 | 7/2015 |
| WO | 2018065831 | 4/2018 |

OTHER PUBLICATIONS

PCT/IB2018/057342, "International Search Report", dated Dec. 27, 2018, 3 pages.

Andrade Alexey S et al , "Alpha-lipoic acid restores tear production in animal model of dry eye." From Experimental eye research Academic press ltd,London,vol. 120,Jan. 4, 2014,pp. 1-9.

* cited by examiner

COMPOSITIONS AND METHODS FOR THE TREATMENT OF EYE DISORDERS

PRIORITY

The present application is a continuation of International Patent Application No. PCT/IB2018/057342, which was filed Sep. 22, 2018, which claims the benefit of Indian Provisional Application No. IN201741041231 filed on Nov. 17, 2017, the contents of which are incorporated in their entirety herein by reference.

TECHNICAL FIELD

The present disclosure generally relates to compounds and compositions for the treatment of eye disorders. More particularly, the present disclosure relates to new compounds and crystals, solvates, enantiomers, stereoisomers, esters, polymorphs, co-crystals and hydrates thereof that can find utility in management of eye disorders. Aspects of the present disclosure also relates to treatment of subjects with a pharmaceutically acceptable dose of compound(s), crystals, solvates, enantiomer, stereoisomer, esters, hydrates, or mixtures thereof.

BACKGROUND

Background description includes information that may be useful in understanding the present invention. It is not an admission that any of the information provided herein is prior art or relevant to the presently claimed invention, or that any publication specifically or implicitly referenced is prior art.

Age-related eye diseases, in many cases are not sudden but tend to develop slowly as a person ages. Of many age-related eye diseases, there are four major diseases that are recognized, which can be detected and treated if a comprehensive eye examination is performed. These four age-related eye diseases—Macular Degeneration, Cataract, Glaucoma and Diabetic Retinopathy are expected to dramatically increase if left untreated and can cause vision loss and blindness. Population that is most at risk for developing eye disease is unaware of the factors that make them susceptible. As the proportion of the elderly population increases around the world, the prevalence and effects of age-related eye diseases are also increasing. The leading causes of blindness and low vision are primarily age-related eye diseases such as age-related macular degeneration, cataract, diabetic retinopathy, and glaucoma. Age-related cataract will become an even larger percentage of the causes of blindness worldwide, and glaucoma and age-related macular degeneration will emerge as public health issues.

Most common eye problems include Refractive errors, Cataracts—clouded lenses, Optic nerve disorders, including glaucoma, Retinal disorders—problems with the nerve layer at the back of the eye, Macular degeneration—a disease that destroys sharp, central vision, Diabetic eye problems and Conjunctivitis—an infection also known as pinkeye. Presbyopia is progressive loss of accommodation resulting in loss of visual ability to focus on objects located at different distances. Accommodation in humans is performed by ciliary muscle and iris sphincter contractions, convergence and changes in the shape and position of the lens. The latter action is passive, meaning the lens changes are dependent on the ciliary muscle and iris contractions. Also, when the centre of the accommodation is active, the ciliary muscle contraction is stimulated and miosis and convergence occurs in normal binocular patients.

Published WO document WO2018065831 (Intl. Appl. No. PCT/IB2017/052237) discloses pilocarpine-(R)-lipoate for treatment of Xerostomia, Sjogrens Syndrome and Dry Mouth, contents of which are incorporated in its entirety herein by reference. However, it fails to suggest utility thereof in treatment of eye disorders and complications associated therewith.

Managing acute pathology often relies on the addressing the underlying pathology and symptoms of the disease. There is currently a need in the art for new compounds and compositions that can find utility in the treatment of eye disorders and/or in delaying the onset of eye disorders and complications associated therewith.

OBJECTS OF THE INVENTION

An object of the present disclosure is to provide compounds and crystals, co-crystals, solvates, enantiomer, stereoisomer, esters, hydrates, or mixtures thereof that can find utility in treatment of eye disorders.

Another object of the present disclosure is to provide a pharmaceutical composition for treatment of eye disorders.

SUMMARY

The present disclosure generally relates to compounds and compositions for the treatment of eye disorders. More particularly, the present disclosure relates to compounds and pharmaceutically acceptable salts, hydrates, solvates, crystals, co-crystals, enantiomers, stereoisomers, esters, polymorphs or prodrugs thereof that can find utility in treatment of eye disorders. Aspects of the present disclosure also relates to treatment of subjects with a pharmaceutically acceptable dose of the compound or pharmaceutically acceptable salts, crystals, solvates, enantiomer, stereoisomer, esters or hydrates thereof.

An aspect of the present disclosure provides a compound of formula I,

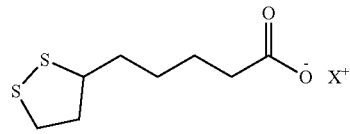

Formula I or a pharmaceutically acceptable hydrate, solvate, crystal, co-crystal, enantiomer, stereoisomer, polymorph or prodrug thereof, wherein, $X^+$ represents,

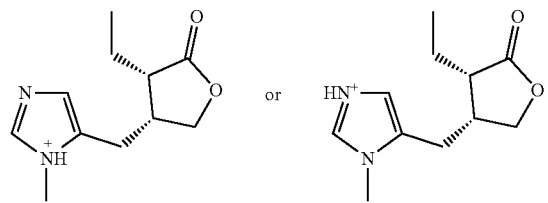

wherein said compound finds use in treatment of eye disorder or complications associated therewith. The eye disorder that can be treated by the compound of formula I of the present disclosure includes macular degeneration, cataract, glaucoma, diabetic retinopathy, dry eye, ocular neuritis, retinitis pigmentosa and presbyopia.

In an embodiment, the compound of formula I can be pilocarpine-RS-lipoate which is selected from:

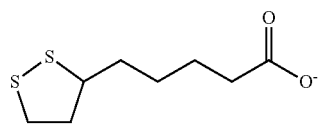

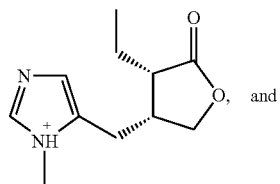
and

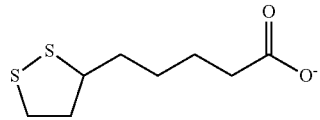

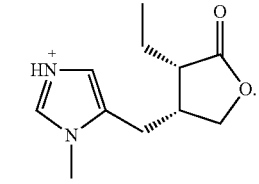

In another embodiment, the compound of Formula I can be pilocarpine-(R)-lipoate which is selected from:

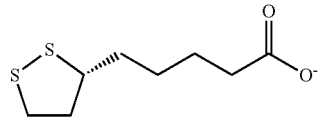

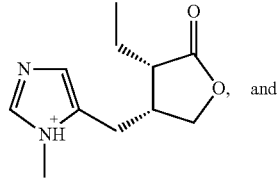
and

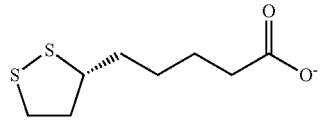

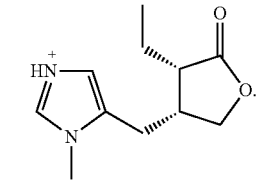

In another embodiment, the compound of Formula I can be pilocarpine-(S)-lipoate which is selected from:

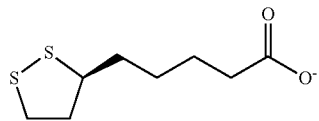

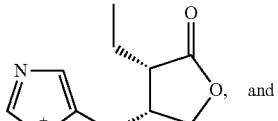
and

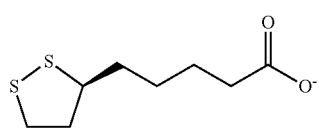

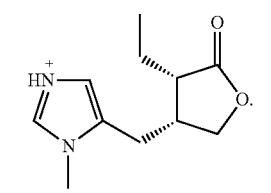

In an embodiment, the compound of Formula I comprises pilocarpine-(R)-lipoate with an enantiomeric excess (ee) of at least 1%. In an embodiment, the compound of Formula I comprises pilocarpine-(S)-lipoate with an enantiomeric excess (ee) of at least 1%.

In an embodiment, the compound of formula I is any of

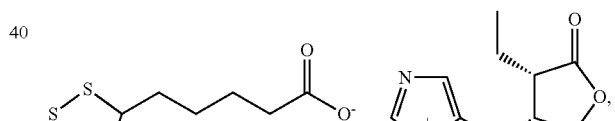

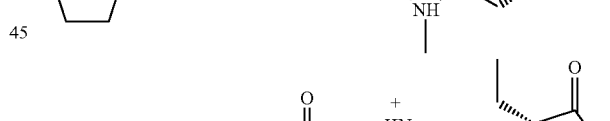

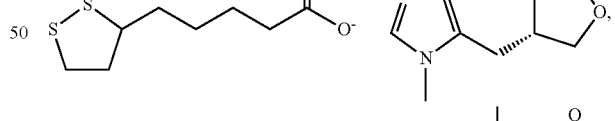

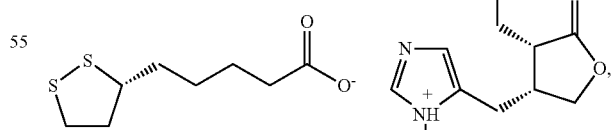

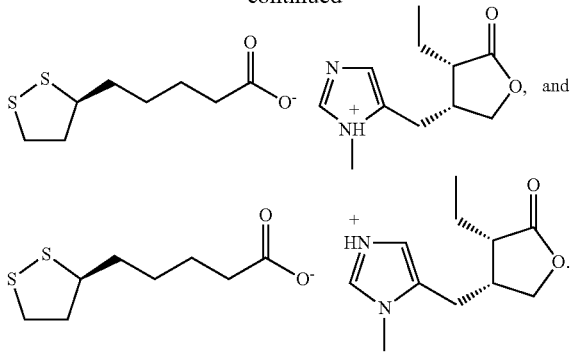
and

Another aspect of the present disclosure is directed to a pharmaceutical composition for treating an eye disorder or complications thereof, which comprises a compound of formula I or a pharmaceutically acceptable hydrate, solvate, crystal, co-crystal, enantiomer, stereoisomer, polymorph or prodrug thereof and a pharmaceutically acceptable excipient. In an embodiment, the pharmaceutical composition is formulated for oral, nasal, topical, rectal, vaginal, aerosol or parenteral administration. In certain preferred embodiments, the pharmaceutical composition is a topical ophthalmic formulation. In certain preferred embodiments, the pharmaceutical composition is an ophthalmic drop formulation.

Another aspect of the present disclosure provides a method of synthesis of pilocarpine-lipoate, the method comprising: treating pilocarpine with lipoic acid at a suitable temperature to obtain pilocarpine-lipoate. In an embodiment, the method further comprises a step of contacting pilocarpine HCl with a base to obtain pilocarpine. In an embodiment, the method comprises treating pilocarpine HCl in a solvent with a base to obtain pilocarpine. In an embodiment, the method comprises treating pilocarpine HCl in acetone with sodium hydrogen carbonate for about 18 h at room temperature to obtain pilocarpine. In an embodiment, the method effects yield of about 100%. In an embodiment, the method further comprises a step of effecting recrystallization of the pilocarpine-lipoate. In an embodiment, the step of effecting recrystallization comprises effecting recrystallization of pilocarpine-lipoate with ethyl acetate (5 volumes) at 50-55° C. to obtain crystalline pilocarpine-lipoate with yield of about 80%.

Another aspect of the present disclosure provides a method of treating an eye disorder or complications thereof in a subject in need thereof, the method comprising administering to the subject a therapeutically effective amount of the compound of formula I disclosed herein or a pharmaceutically acceptable hydrate, solvate, crystal, co-crystal, enantiomer, stereoisomer, polymorph or prodrug thereof. In an embodiment, the eye disorder that can be treated by the method disclosed herein can include macular degeneration, cataract, glaucoma, diabetic retinopathy, dry eye, ocular neuritis, retinitis pigmentosa and presbyopia.

In yet another aspect, the present disclosure is directed to use of the compound of formula I or a pharmaceutically acceptable hydrate, solvate, crystal, co-crystal, enantiomer, stereoisomer, polymorph or prodrug thereof for manufacture of a medicament for treatment of an eye disorder or complications associated therewith.

Various objects, features, aspects and advantages of the inventive subject matter will become more apparent from the following detailed description of preferred embodiments, along with the accompanying drawing figures in which like numerals represent like components.

DETAILED DESCRIPTION

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms as used herein are shown below. To the extent a term used in a claim is not defined below, it should be given the broadest definition persons in the pertinent art have given that term as reflected in printed publications and issued patents at the time of filing.

The term "isomers" as used herein throughout the present disclosure encompasses within its meaning, the compounds that have same molecular formula but differ in the nature or sequence of bonding of their atoms or arrangement of their atoms in space.

The term "stereoisomer" as used herein throughout the present disclosure encompasses within its meaning, isomers that differ in the arrangement of their atoms in space.

The term "diastereomer" as used herein throughout the present disclosure encompasses within its meaning, stereoisomers with opposite configuration at one or more chiral centers, which are not enantiomers.

The term "enantiomer" as used herein throughout the present disclosure encompasses within its meaning, stereoisomers bearing one or more asymmetric centers that are non-superimposable mirror images of each other. When a compound has one asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog (CIP), or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" as used herein is art-recognized and refers to a crystal structure of a given compound.

The phrases "parenteral administration" and "administered parenterally" as used herein refer to modes of administration other than enteral and topical administration, such as injections, and include intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion, but not limited thereto.

A "patient," "subject," or "host" to be treated by the subject method may mean either a human or non-human animal, such as primates, mammals, and vertebrates.

The phrase "pharmaceutically acceptable" is art-recognized. In certain embodiments, the term includes compositions, polymers and other materials and/or dosage forms which are, within the scope of sound medical judgment, suitable for use in contact with the tissues of mammals, human beings and animals without excessive toxicity, irritation, allergic response, or other problem or complication, commensurate with a reasonable benefit/risk ratio.

The phrase "pharmaceutically acceptable excipient" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "prodrug" is intended to encompass compounds that, under physiological conditions, are converted into the therapeutically active agents of the present disclosure. A common method for making a prodrug is to include selected moieties that are hydrolyzed under physiological conditions to reveal the desired molecule. In other embodiments, the prodrug is converted by an enzymatic activity of the host animal.

The term "prophylactic or therapeutic" treatment is art-recognized and includes administration to the host of one or more of the compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e. it is intended to diminish, ameliorate, or stabilize the existing unwanted condition or side effects thereof).

The term "treating" or "treatment" is art recognized and includes preventing a disease, disorder or condition from occurring in a human being or an animal, which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating Disorders of eyelid, lacrimal system and orbit, Disorders of conjunctiva, Disorders of sclera, cornea, iris and ciliary body, Disorders of lens, Disorders of choroid and retina, Glaucoma, Disorders of vitreous body and globe, Disorders of optic nerve and visual pathways, Visual disturbances and blindness, Presbyopia and other related diseases or any other medical condition, is well understood in the art, and includes administration of a composition which reduces the frequency of, or delays the onset of, symptoms of a medical condition in a subject relative to a subject which does not receive such composition.

The phrase "therapeutically effective amount" is an art-recognized term. In certain embodiments, the term refers to an amount of a solvate or hydrate or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

As used herein, the term "ophthalmic composition" refers to a composition intended for application to the eye or its related or surrounding tissues such as, for example, the eyelid or onto the cornea. The term also includes compositions intended to therapeutically treat conditions of the eye itself or the tissues surrounding the eye. The ophthalmic composition can be applied topically or by other techniques, as known to or appreciated by persons skilled in the pertinent art, such as injection to the eye. Examples of suitable topical administration to the eye include administration in form of eye drops and by spray formulations. A further suitable topical administration route is by subconjunctival injection. The compositions can also be provided to the eye periocularly or retro-orbitally.

In certain embodiments, the pharmaceutical compositions described herein are formulated in a manner such that said compositions will be delivered to a patient in a therapeutically effective amount, as part of a prophylactic or therapeutic treatment. The desired amount of the composition to be administered to a patient will depend on absorption, inactivation, and excretion rates of the drug as well as the delivery rate of the hydrates or solvates and compositions from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Additionally, the optimal concentration and/or quantities or amounts of any particular solvate or hydrate or composition may be adjusted to accommodate variations in the treatment parameters. Such treatment parameters include the clinical use to which the preparation is put, e.g., the site treated, the type of patient, e.g., human or non-human, adult or child, and the nature of the disease or condition.

In certain embodiments, the dosage of the compounds of Formula I provided herein may be determined by reference to the plasma concentrations of the therapeutic composition or other encapsulated materials. For example, the maximum plasma concentration (Cmax) and the area under the plasma concentration-time curve from time 0 to infinity may be used.

When used with respect to a pharmaceutical composition or other material, the term "sustained release" is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, mucus secretions, lymph or the like, one or more of the pharmaceutically acceptable excipients may undergo gradual or delayed degradation (for example, through hydrolysis) with concomitant release of any material incorporated therein, e.g., an therapeutic and/or biologically active solvate or hydrate and/or composition, for a sustained or extended period (as compared to the release from a bolus). This release may result in prolonged delivery of therapeutically effective amounts of any of the therapeutic agents (compounds) disclosed herein.

The phrases "systemic administration," "administered systemically," "peripheral administration" and "administered peripherally" are art-recognized, and include the administration of a subject composition, therapeutic or other material at a site remote from the disease being treated. Administration of an agent for the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The present disclosure also contemplates prodrugs of the compositions disclosed herein, as well as pharmaceutically acceptable hydrates or solvates of said prodrugs.

The present disclosure generally relates to compounds and compositions for the treatment of eye disorders. More particularly, the present disclosure relates to compounds and pharmaceutically acceptable crystals, co-crystals, solvates, enantiomers, stereoisomers, prodrugs or hydrates thereof that can find utility in treatment of eye disorders. Aspects of the present disclosure also relate to methods of treating an eye disorder and/or complications thereof in a subject in need thereof.

An aspect of the present disclosure provides a compound of formula I,

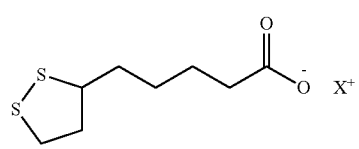

Formula I or a pharmaceutically acceptable hydrate, solvate, crystal, co-crystal, enantiomer, stereoisomer, polymorph or prodrug thereof, wherein, $X^+$ represents,

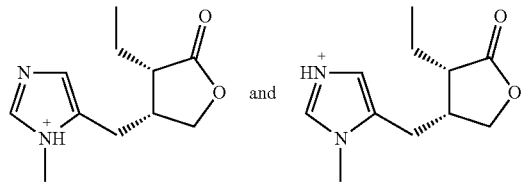

wherein said compound finds use in treatment of eye disorder or complications associated therewith. The eye disorder that can be treated by the compound of formula I of the present disclosure includes macular degeneration, cataract, glaucoma, diabetic retinopathy, dry eye, ocular neuritis, retinitis pigmentosa and presbyopia.

In an embodiment, the compound of formula I can be pilocarpine-RS-lipoate which is selected from:

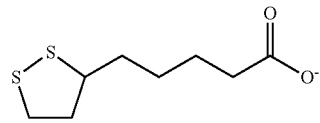

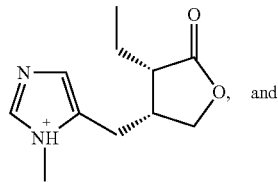

and

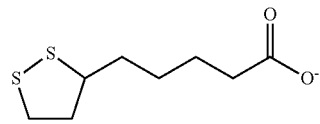

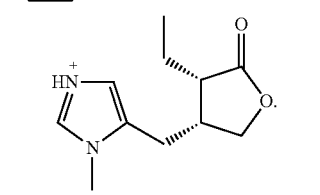

In an embodiment, the compound of Formula I can be pilocarpine-(R)-lipoate which is selected from:

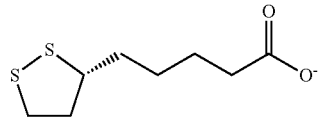

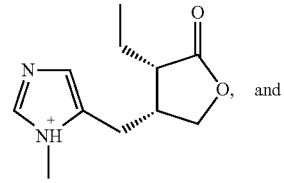, and

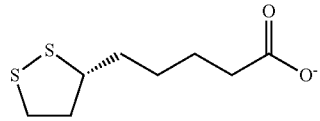

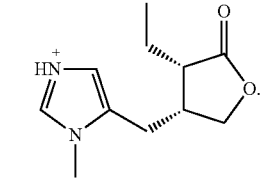

In an embodiment, the compound of Formula I can be pilocarpine-(S)-lipoate which is selected from:

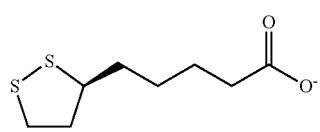

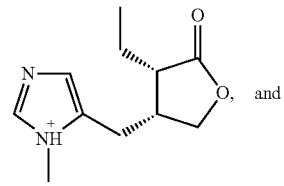, and

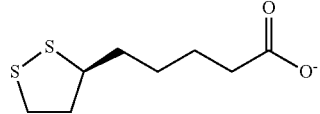

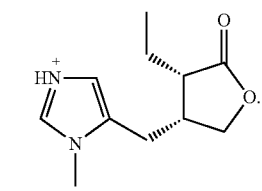

In an embodiment, the compound of Formula I comprises pilocarpine-(R)-lipoate with an enantiomeric excess (ee) of at least 1%. In an embodiment, the compound of Formula I comprises pilocarpine-(S)-lipoate with an enantiomeric excess (ee) of at least 1%.

In an embodiment, the compound of formula I is any of

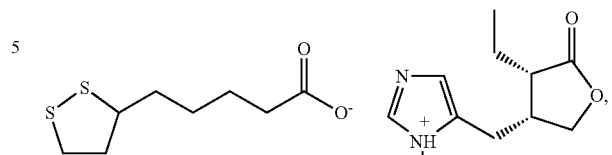

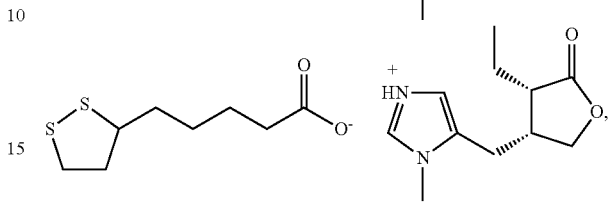

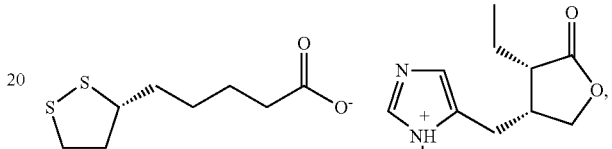

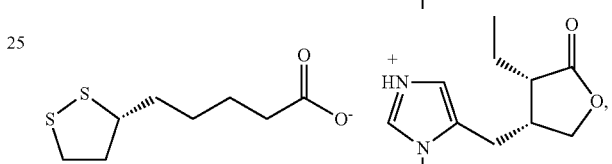

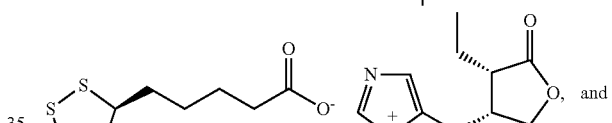, and

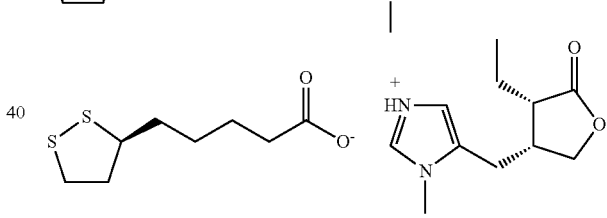

Another aspect of the present disclosure is directed to a pharmaceutical composition for treating an eye disorder or complications thereof, which comprises the disclosed compound of formula I or a pharmaceutically acceptable hydrate, solvate, crystal, co-crystal, enantiomer, stereoisomer, polymorph or prodrug thereof and a pharmaceutically acceptable excipient. In an embodiment, the pharmaceutical composition is formulated for oral, nasal, topical, rectal, vaginal, aerosol or parenteral administration. In certain preferred embodiments, the pharmaceutical composition is a topical ophthalmic formulation. In certain preferred embodiments, the pharmaceutical composition is an ophthalmic drop formulation.

Another aspect of the present disclosure provides a method of synthesis of pilocarpine-lipoate, the method comprising: treating pilocarpine with lipoic acid at a suitable temperature to obtain pilocarpine-lipoate. In an embodiment, the method further comprises a step of contacting pilocarpine HCl with a base to obtain pilocarpine. In an embodiment, the method comprises treating pilocarpine HCl in a solvent with a base to obtain pilocarpine. In an embodiment, the method comprises treating pilocarpine HCl in acetone with sodium hydrogen carbonate for about 18 h at room temperature to obtain pilocarpine. In an embodiment, the method effects yield of about 100%. In an embodiment, the method further comprises a step of effecting recrystallization of the pilocarpine-lipoate. In an embodiment, the step of effecting recrystallization comprises effecting recrystallization of pilocarpine-lipoate with ethyl acetate (5 volumes) at 50-55° C. to obtain crystalline pilocarpine-lipoate with yield of about 80%.

Another aspect of the present disclosure provides a method of synthesis of pilocarpine-(R)-lipoate, the method comprising: contacting pilocarpine with (R)-lipoic acid at a suitable temperature to obtain pilocarpine-(R)-lipoate. In an embodiment, the method comprises contacting pilocarpine HCl with a base to obtain pilocarpine. In an embodiment, the method comprises treating pilocarpine HCl in a solvent with a base to obtain pilocarpine. In an embodiment, the method comprises treating pilocarpine HCl in acetone with sodium hydrogen carbonate for about 18 h at room temperature to obtain pilocarpine. In an embodiment, the method effects yield of about 100%. However, a person skilled in the pertinent art would appreciate that any other method of synthesis of pilocarpine-(R)-lipoate, as known to or appreciated by a person skilled in the art, can be suitably employed to sub-serve its intended purpose without departing from the scope and spirit of the present disclosure.

In an embodiment, the method further comprises a step of effecting recrystallization of the pilocarpine-(R)-lipoate. In an embodiment, the step of effecting recrystallization comprises effecting recrystallization of pilocarpine-(R)-lipoate with ethyl acetate (5 volumes) at 50-55° C. to obtain crystalline pilocarpine-(R)-lipoate with yield of about 80%. However, it should be appreciated that recrystallization of the pilocarpine-(R)-lipoate can be effected employing any other method as known to or appreciated by a person skilled in the pertinent art without departing from the scope and spirit of the present invention.

Although several embodiments of the present disclosure describes the method of preparation and recrystallization of pilocarpine-(R)-lipoate, it should be appreciated by a person skilled in the art, the substantially same or similar method can be used for synthesis of pilocarpine-(R,S)-lipoate and/or pilocarpine-(S)-lipoate and the same has not been described in detail for the sake of brevity.

Still further aspect of the present disclosure provides a method of treating an eye disorder or complications thereof in a subject in need thereof, the method comprising administering to the subject a therapeutically effective amount of the compound of formula I or a pharmaceutically acceptable hydrate, solvate, crystal, co-crystal, enantiomer, stereoisomer, polymorph or prodrug thereof. In an embodiment, the eye disorder that can be treated by the method disclosed herein can include macular degeneration, cataract, glaucoma, diabetic retinopathy, dry eye, ocular neuritis, retinitis pigmentosa and presbyopia. In an embodiment, the compound of formula I can be administered to said subject in combination with a pharmaceutically acceptable excipient. In an embodiment, the therapeutically effective amount of the compound of formula I that can be administered to said subject can range from 0.001 mg to 1000 mg. In an embodiment, the compound of formula I can be administered topically to at least one eye of a subject in need of treatment for eye disorder or complications associated therewith.

In an embodiment, the compound of formula I that can be used in the treatment method of the present disclosure can be selected from one or more of:

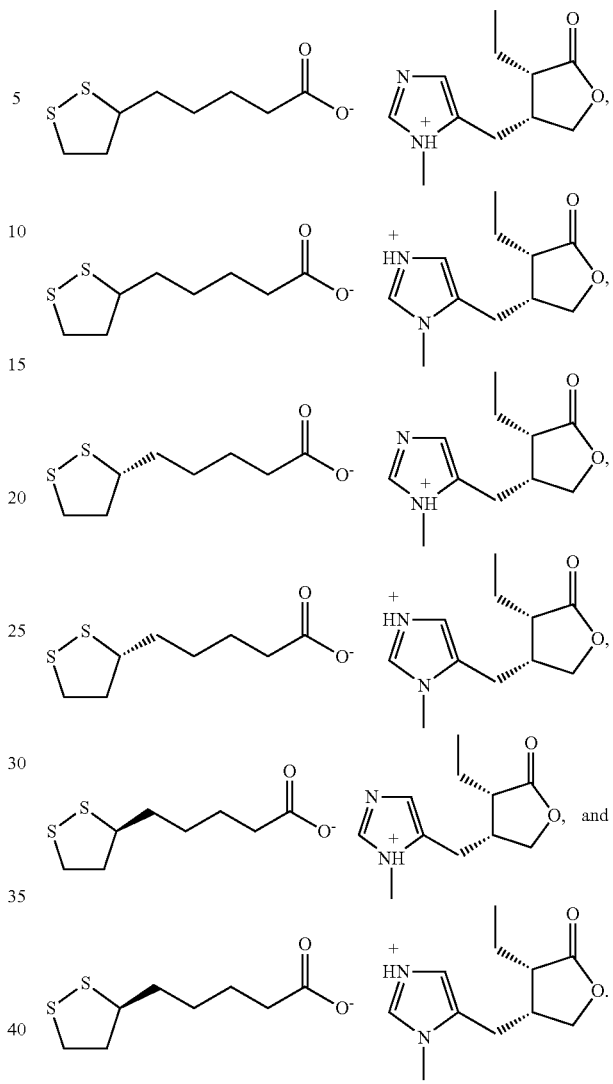

The compounds of the present disclosure may be in the form of hydrates or solvates of acid moiety—lipoic acid and the base component represented as X+ in which the acid component is in partially ionic form and the base component represented as X+ is protonated in the pharmaceutically acceptable salt. In some instances, however, for example depending on the pH of the environment, the compounds may be in the form of a mixture of X+ and lipoic acid.

Without wishing to bound by the theory, it is believed that pilocarpine aids in lowering intraocular pressure, induces miosis and assists in accommodation in the eye, while lipoic acid acts as an anti-oxidant, regenerates glutathione and improves lens activity in the human eye.

Synthesis of Compounds of Formula I

Pilocarpine salt in a solvent can be treated with a base for a time period to get free base of pilocapine, which upon contact with lipoic acid results in formation of compounds of Formula I. Alternatively, pilocarpine can be contacted with lipoic acid to directly obtain compounds of Formula I. A person skilled in the pertinent art would appreciate that choice of solvent, base and process parameters like temperature, time and the likes can be suitably amended/ selected in order to sub-serve its intended purpose and the scope of the present disclosure is not restricted to utilization of any specific solvent/base and/or the process parameters.

In an embodiment, firstly, pilocarpine HCl in acetone is treated with sodium hydrogen carbonate for 18 h at room temperature to get free base of Pilocarpine, which upon reaction with (R)-Lipoic acid at room temperature for 1 h gives Pilocarpine-(R)-Lipoate in about 100% yield.

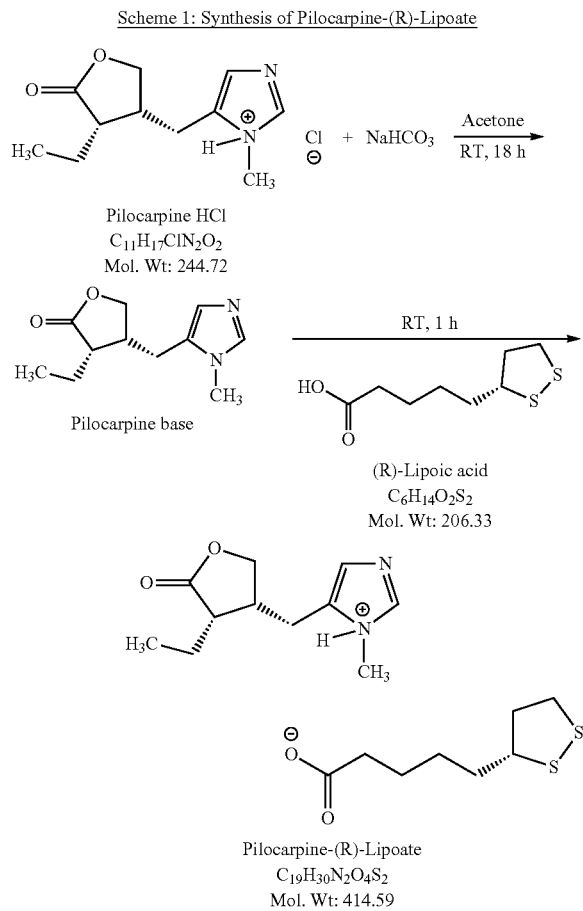

Scheme 1: Synthesis of Pilocarpine-(R)-Lipoate

In an embodiment, the pilocarpine-lipoate is recrystallized using suitable solvent or a combination of solvents to afford crystalline Pilocarpine-Lipoate. Such solvent or combination of solvents are well known to a person skilled in the pertinent art and same has not been described in detail for the sake of clarity. The technique of recrystallization is elaborately dealt with in "Remington—The Science and Practice of Pharmacy", 20th. Ed., Lippincott Williams & Wilkins, Baltimore, Md., 2000", contents of which are incorporated herein in its entirety by way of reference. In an embodiment, Pilocarpine-(R)-Lipoate is recrystallized from ethyl acetate (5 volumes) at 50-55° C. to afford yellow crystalline Pilocarpine-(R)-Lipoate in about 80% yield.

The present disclosure also discloses pharmaceutical compositions comprising a pharmaceutically acceptable excipient and one or a combination of compounds of Formula I that may be formulated for systemic or topical or oral administration. The pharmaceutical composition may be also formulated for oral administration, oral solution, injection, subdermal administration, or transdermal administration.

In many embodiments, the pharmaceutical compositions described herein incorporate the disclosed compounds (Formula I) to be delivered in an amount sufficient to deliver to a patient, a therapeutically effective amount of a compound of Formula I, as part of a prophylactic or therapeutic treatment. The desired concentration of compound(s) of Formula I or its pharmaceutical acceptable hydrates or solvates will depend on absorption, inactivation, and excretion rates of the drug as well as the delivery rate of the hydrates or solvates and compositions from the subject compositions. It is to be noted that dosage values may also vary with the severity of the condition to be alleviated. It is to be further understood that for any particular subject, specific dosage regimens may need to be adjusted over time according to the individual need and the professional judgment of the person administering or supervising the administration of the compositions. Typically, dosing will be determined using techniques known to one skilled in the art.

Additionally, the optimal concentration and/or quantities or amounts of any particular compound of Formula I may be adjusted to accommodate variations in the treatment parameters. Such treatment parameters may include the clinical use to which the preparation is put, e.g., the site treated, the type of patient, e.g., human or non-human, adult or child, and the nature of the disease or condition, but not limited thereto.

The concentration and/or amount of any compound of Formula I may be readily identified by routine screening in animals, e.g., rats, by screening a range of concentration and/or amounts of the material in question using appropriate assays. Known methods are also available to assay local tissue concentrations, diffusion rates of the hydrates or solvates or compositions, and local blood flow before and after administration of therapeutic formulations disclosed herein. One such method is microdialysis, as reviewed by T. E. Robinson et al., 1991, microdialysis in the neurosciences, Techniques, volume 7, Chapter 1. The methods reviewed by Robinson may be applied, in brief, as follows. A microdialysis loop is placed in situ in a test animal. Dialysis fluid is pumped through the loop. When compounds with Formula I such as those disclosed herein are injected adjacent to the loop, released drugs are collected in the dialysate in proportion to their local tissue concentrations. The progress of diffusion of the hydrates or solvates or compositions may be determined thereby with suitable calibration procedures using known concentrations of hydrates or solvates or compositions.

In certain embodiments, the dosage of the compounds of Formula I provided herein may be determined by reference to the plasma concentrations of the composition or other encapsulated materials. For example, the maximum plasma concentration (Cmax) and the area under the plasma concentration-time curve from time 0 to infinity may be used.

Generally, in carrying out the methods detailed in the present disclosure, an effective dosage for the compound of Formula I is in the range of about 0.01 mg/kg/day to about 100 mg/kg/day in single or divided doses, for instance 0.01 mg/kg/day to about 50 mg/kg/day in single or divided doses. The compounds of Formulas I may be administered at a dose of, for example, less than 0.2 mg/kg/day, 0.5 mg/kg/day, 1.0 mg/kg/day, 5 mg/kg/day, 10 mg/kg/day, 20 mg/kg/day, 30 mg/kg/day, or 40 mg/kg/day. Compound of Formula I may also be administered to a human patient at a dose of, for example, between 0.001 mg and 1000 mg, between 5 mg and 80 mg, or less than 1.0, 9.0, 12.0, 20.0, 50.0, 75.0, 100, 300, 400, 500, 800, 1000, 2000, 5000 mg per day. In certain embodiments, the compositions herein are administered at an amount that is less than 95%, 90%, 80%, 70%, 60%, 50%, 40%, 30%, 20%, or 10% of the compound of Formula I required for the same therapeutic benefit.

A therapeutically effective amount of the compound of Formula I as described herein refers to an amount of the compound of formula I which is sufficient to elicit the desired biological response. An effective amount may be sufficient to prohibit, treat, alleviate, ameliorate, halt, restrain, slow or reverse the progression, or reduce the severity of a complication resulting from intraocular pressure, optic nerve complications, glaucoma, ocular lens complications, cataracts, lens thickening and refractive index problems of the eye. As such, these methods include both medical therapeutic (acute) and/or prophylactic (prevention) administration as appropriate. The amount and timing of compositions administered will, of course, be dependent on the subject being treated, on the severity of the affliction, on the manner of administration and on the judgment of the prescribing physician. Thus, because of patient-to-patient variability, the dosages given above are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases. In an exemplary embodiment, the therapeutically effective amount of the compound of Formula I can range from 0.001 mg to 1000 mg.

The compositions disclosed herein may be administered to a subject in need of treatment by a variety of conventional routes of administration, including orally, topically, parenterally, e.g., intravenously, subcutaneously or intramedullary, but not limited thereto. Further, the compositions may be administered intranasally, as a rectal suppository, or using a "flash" formulation, i.e., allowing the medication to dissolve in the mouth without the need to use water. Furthermore, the compositions may be administered to a subject in need of treatment by controlled release dosage forms, site specific drug delivery, transdermal drug delivery, patch (active/passive) mediated drug delivery, by stereotactic injection, or in nanoparticles.

The compositions may be administered alone or in combination with pharmaceutically acceptable carriers, vehicles or diluents (collectively, referred to herein as excipients), in either single or multiple doses. Suitable pharmaceutical carriers, vehicles and diluents include inert solid diluents or fillers, sterile aqueous solutions and various organic solvents. The pharmaceutical compositions formed by combining the compounds and the pharmaceutically acceptable carriers, vehicles or diluents are then readily administered in a variety of dosage forms such as tablets, powders, lozenges, syrups, injectable solutions and the likes. These pharmaceutical compositions may, if desired, contain additional ingredients such as flavorings, binders, excipients and the likes. Thus, for purposes of oral administration, tablets containing various excipients such as L-arginine, sodium citrate, calcium carbonate and calcium phosphate may be employed along with various disintegrating agents such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Appropriate materials for this include lactose or milk sugar and high molecular weight polyethylene glycols, but not limited thereto. When aqueous suspensions or elixirs are desired for oral administration, the essential active ingredient may be combined with various sweetening or flavoring agents, coloring matter or dyes and, if desired, emulsifying or suspending agents, together with diluents such as water, ethanol, propylene glycol, glycerin and combinations thereof. The compounds of Formula I may also be formulated as enterically coated formulations including various excipients, as is well known in the pharmaceutical art.

For parenteral administration, solutions (compositions) may be prepared using (for example) sesame or peanut oil, aqueous propylene glycol, or sterile aqueous solutions. Such solutions may be suitably buffered if necessary, and the liquid diluent is first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The formulations, for instance tablets, may contain e.g. 10 to 100, 50 to 250, 150 to 500 mg, or 350 to 800 mg e.g. 10, 50, 100, 300, 500, 700, 800 mg of the compounds of Formula I disclosed herein, for instance, compounds of Formula I or pharmaceutical acceptable hydrates or solvates of a compounds of Formula I.

Generally, a composition as described herein may be administered orally, or parenterally (e.g., intravenous, intramuscular, subcutaneous or intramedullary). Topical administration may also be indicated, for example, where the patient is suffering from gastrointestinal disorder that prevent oral administration, or whenever the medication is best applied to the surface of a tissue or organ as determined by the attending physician. Localized administration may also be indicated, for example, when a high dose is desired at the target tissue or organ. For buccal administration the active composition may take the form of tablets or lozenges formulated in a conventional manner.

The dosage administered will be dependent upon the identity of the disease; the type of host involved, including its age, health and weight; the kind of concurrent treatment, if any; the frequency of treatment and therapeutic ratio, but not limited thereto. Illustratively, dosage levels of the administered active ingredients are: ocular, 0.0001 to about 100 mg/kg; intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions, suspensions, and oral solutions or suspensions and the like, containing suitable quantities of an active ingredient. For oral administration either solid or fluid unit dosage forms can be prepared.

As discussed above, the tablet core may contain one or more hydrophilic polymers. Suitable hydrophilic polymers include, but are not limited to, water swellable cellulose derivatives, polyalkylene glycols, thermoplastic polyalkylene oxides, acrylic polymers, hydrocolloids, clays, gelling starches, swelling cross-linked polymers, and mixtures thereof. Examples of suitable water swellable cellulose derivatives include, but are not limited to, sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols include, but are not limited to, polyethylene glycol. Examples of suitable thermoplastic polyalkylene oxides include, but are not limited to, poly(ethylene oxide). Examples of suitable acrylic polymers include, but are not limited to, potassium methacrylatedivinylbenzene copolymer, polymethylmethacrylate, high-molecular weight crosslinked acrylic acid homopolymers and copolymers such as those commercially available from Noveon Chemicals under the tradename CARBOPOL™. Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof. Examples of suitable clays include, but are not limited to, smectites such as bentonite, kaolin, and laponite; magnesium trisilicate; magnesium aluminum silicate; and mixtures thereof. Examples of suitable gelling starches include, but are not limited to, acid hydrolyzed starches, swelling starches such as sodium starch glycolate and derivatives thereof, and mixtures thereof. Examples of suitable swelling cross-linked polymers include, but are not limited to, cross-linked polyvinyl pyrrolidone, cross-linked agar, and cross-linked carboxymethylcellulose sodium, and mixtures thereof.

The carrier may contain one or more suitable excipients for the formulation of tablets. Examples of suitable excipients include, but are not limited to, fillers, adsorbents, binders, disintegrants, lubricants, glidants, release-modifying excipients, superdisintegrants, antioxidants or mixtures thereof.

Suitable binders include, but are not limited to, dry binders such as polyvinyl pyrrolidone and hydroxypropylmethylcellulose; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, and starches; and mixtures thereof. Suitable disintegrants include, but are not limited to, sodium starch glycolate, cross-linked polyvinylpyrrolidone, cross-linked carboxymethylcellulose, starches, microcrystalline cellulose, and mixtures thereof. Suitable lubricants include, but are not limited to, long chain fatty acids and their hydrates or solvates, such as magnesium stearate and stearic acid, talc, glycerides waxes, and mixtures thereof. Suitable glidants include, but are not limited to, colloidal silicon dioxide. Suitable release-modifying excipients include, but are not limited to, insoluble edible materials, pH-dependent polymers, and mixtures thereof.

Suitable insoluble edible materials for use as release-modifying excipients include, but are not limited to, water-insoluble polymers and low-melting hydrophobic materials, copolymers thereof, and mixtures thereof. Examples of suitable water-insoluble polymers include, but are not limited to, ethylcellulose, polyvinyl alcohols, polyvinyl acetate, polycaprolactones, cellulose acetate and its derivatives, acrylates, methacrylates, acrylic acid copolymers, copolymers thereof and mixtures thereof. Suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their hydrates or solvates, and mixtures thereof. Examples of suitable fatty acid esters include, but are not limited to, sucrose fatty acid esters, mono-, di-, and triglycerides, glyceryl behenate, glyceryl palmitostearate, glyceryl monostearate, glyceryl tristearate, glyceryl trilaurylate, glyceryl myristate, Glyco-Wax-932, lauroyl macrogol-32 glycerides, stearoyl macrogol-32 glycerides, and mixtures thereof. Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, and paraffin wax; fat-containing mixtures such as chocolate, and mixtures thereof. Examples of super disintegrants include, but are not limited to, croscarmellose sodium, sodium starch glycolate and cross-linked povidone (crospovidone). In one embodiment the tablet core contains up to about 5 percent by weight of such super disintegrant.

Examples of antioxidants include, but are not limited to, tocopherols, ascorbic acid, sodium pyrosulfite, butylhydroxytoluene, butylated hydroxyanisole, edetic acid, and edetate hydrates or solvates, and mixtures thereof. Examples of preservatives include, but are not limited to, citric acid, tartaric acid, lactic acid, malic acid, acetic acid, benzoic acid, and sorbic acid, and mixtures thereof.

In one embodiment, the immediate release coating has an average thickness of at least 50 microns, such as from about 50 microns to about 2500 microns; e.g., from about 250 microns to about 1000 microns. In embodiment, the immediate release coating is typically compressed at a density of more than about 0.9 g/cc, as measured by the weight and volume of that specific layer.

In one embodiment, the immediate release coating contains a first portion and a second portion, wherein at least one of the portions contains the second pharmaceutically active agent. In one embodiment, the portions contact each other at a center axis of the tablet. In one embodiment, the first portion includes the first pharmaceutically active agent and the second portion includes the second pharmaceutically active agent.

In one embodiment, the first portion contains the first pharmaceutically active agent and the second portion contains the second pharmaceutically active agent. In one embodiment, one of the portions contains a third pharmaceutically active agent. In one embodiment one of the portions contains a second immediate release portion of the same pharmaceutically active agent as that contained in the tablet core.

In one embodiment, the outer coating portion is prepared as a dry blend of materials prior to addition to the coated tablet core. In another embodiment the outer coating portion is included of a dried granulation including the pharmaceutically active agent.

Formulations with different drug release mechanisms described above could be combined in a final dosage form containing single or multiple units. Examples of multiple units include multilayer tablets, capsules containing tablets, beads, or granules in a solid or liquid form. Typical, immediate release formulations include compressed tablets, gels, films, coatings, liquids and particles that can be encapsulated, for example, in a gelatin capsule. Many methods for preparing coatings, covering or incorporating drugs, are known in the art.

The immediate release dosage, unit of the dosage form, i.e., a tablet, a plurality of drug-containing beads, granules or particles, or an outer layer of a coated core dosage form, contains a therapeutically effective quantity of the active agent with conventional pharmaceutical excipients. The immediate release dosage unit may or may not be coated, and may or may not be admixed with the delayed release dosage unit or units (as in an encapsulated mixture of immediate release drug-containing granules, particles or beads and delayed release drug-containing granules or beads).

Extended release formulations are generally prepared as diffusion or osmotic systems, for example, as described in "Remington—The Science and Practice of Pharmacy", 20th. Ed., Lippincott Williams & Wilkins, Baltimore, Md., 2000. A diffusion system typically consists of one of two types of devices, reservoir and matrix, which are well known and described in the art. The matrix devices are generally prepared by compressing the drug with a slowly dissolving polymer carrier into a tablet form.

An immediate release portion can be added to the extended release system by means of either applying an immediate release layer on top of the extended release core; using coating or compression processes or in a multiple unit system such as a capsule containing extended and immediate release beads.

Delayed release dosage formulations are created by coating a solid dosage form with a film of a polymer, which is insoluble in the acid environment of the stomach, but soluble in the neutral or slightly basic environment of small intestine. The delayed release dosage units can be prepared, for example, by coating a drug or a drug-containing composition with a selected coating material. The drug-containing composition may be a tablet for incorporation into a capsule, a tablet for use as an inner core in a "coated core" dosage form, or a plurality of drug-containing beads, particles or granules, for incorporation into either a tablet or capsule.

A pulsed release dosage form is one that mimics a multiple dosing profile without repeated dosing and typically allows at least a twofold reduction in dosing frequency as compared to the drug presented as a conventional dosage form (e.g., as a solution or prompt drug-releasing, conventional solid dosage form). A pulsed release profile is characterized by a time period of no release (lag time) or reduced release followed by rapid drug release.

Each dosage form contains a therapeutically effective amount of active agent (compound of formula I). In one embodiment of dosage forms that mimic a twice daily dosing profile, approximately 30 wt. % to 70 wt. %, preferably 40 wt. % to 60 wt. %, of the total amount of active agent in the dosage form is released in the initial pulse, and, correspondingly approximately 70 wt. % to 30 wt. %, preferably 60 wt. % to 40 wt. %, of the total amount of active agent in the dosage form is released in the second pulse. For dosage forms mimicking the twice daily dosing profile, the second pulse is preferably released approximately 3 hours to less than 14 hours, and more preferably approximately 5 hours to 12 hours, following administration.

Another dosage form contains a compressed tablet or a capsule having a drug-containing immediate release dosage unit, a delayed release dosage unit and an optional second delayed release dosage unit. In this dosage form, the immediate release dosage unit contains a plurality of beads, granules particles that release drug substantially immediately following oral administration to provide an initial dose. The delayed release dosage unit contains a plurality of coated beads or granules, which release drug approximately 3 hours to 14 hours following oral administration to provide a second dose.

For purposes of transdermal (e.g., topical) administration, dilute sterile, aqueous or partially aqueous solutions (usually in about 0.1% to 5% concentration), otherwise similar to the above parenteral solutions, may be prepared.

Methods of preparing various pharmaceutical compositions with a certain amount of one or more compounds of Formula I and/or other active agents are known, or will be apparent in light of this disclosure, to those skilled in this art. For examples of methods of preparing pharmaceutical compositions, see Remington's Pharmaceutical Sciences, Mack Publishing Company, Easton, Pa., 19th Edition (1995).

In addition, in certain embodiments, subject compositions of the present application maybe lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including ophthalmic, buccal and sublingual), rectal, vaginal, aerosol and/or parenteral administration. The formulations may conveniently be presented in unit dosage form and may be prepared by any methods well known in the art of pharmacy. The amount of the compound that may be combined with a carrier material/excipient to produce a single dose may vary depending upon the subject being treated, and the particular mode of administration.

Methods of preparing these formulations or compositions include the step of bringing into association compound with the carrier and, optionally, one or more accessory ingredients. In general, the formulations are prepared by uniformly and intimately bringing into association a compound with liquid carriers, or finely divided solid carriers, or both, and then, if necessary, shaping the product.

The compounds of Formula I described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may for example contain 0.005-90% w/w, for instance 0.005-50%, 0.005-5% w/w, or 0.01-1.0% w/w, of medicament relative to the total weight of the formulation.

In solid dosage forms for oral administration (capsules, tablets, pills, dragees, powders, granules and the like), the subject composition is mixed with one or more pharmaceutically acceptable carriers and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using lactose or milk sugars, as well as high molecular weight polyethylene glycols and the like.

Liquid dosage forms for oral administration include pharmaceutically acceptable emulsions, microemulsions, solutions, suspensions, syrups and elixirs. In addition to the subject compositions, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, corn, peanut, sunflower, soybean, olive, castor, and sesame oils), glycerol, tetrahydrofuryl alcohol, polyethylene glycols and fatty acid esters of sorbitan, and mixtures thereof.

Suspensions, in addition to the active ingredient, may contain suspending agents such as, for example, ethoxylated isostearyl alcohols, polyoxyethylene sorbitol, and sorbitan esters, microcrystalline cellulose, aluminum metahydroxide, bentonite, agar-agar and tragacanth, or mixtures thereof.

Dosage forms for transdermal administration include powders, sprays, ointments, pastes, creams, lotions, gels, solutions, patches, and inhalants. A subject composition may be mixed under sterile conditions with a pharmaceutically acceptable carrier, and with any preservatives, buffers, or propellants that may be required. For transdermal administration, the complexes may include lipophilic and hydrophilic groups to achieve the desired water solubility and transport properties.

The ointments, pastes, creams and gels may contain, in addition to subject compositions, other carriers, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays may contain, in addition to a subject composition, excipients such as lactose, talc, silicic acid, aluminum hydroxide, calcium silicates and polyamide powder, or mixtures of such substances. Sprays may additionally contain customary propellants, such as chlorofluorohydrocarbons and volatile unsubstituted hydrocarbons, such as butane and propane.

Methods of delivering a composition or compositions via a transdermal patch are known in the art. Exemplary patches and methods of patch delivery are described in U.S. Pat. Nos. 6,974,588, 6,564,093, 6,312,716, 6,440,454, 6,267,983, 6,239,180, and 6,103,275.

In another embodiment, a transdermal patch may include: a substrate sheet comprising a composite film formed of a resin composition comprising 100 parts by weight of a polyvinyl chloride-polyurethane composite and 2-10 parts by weight of a styrene-ethylene-butylene-styrene copolymer, a first adhesive layer on the one side of the composite film, and a polyalkylene terephthalate film adhered to the one side of the composite film by means of the first adhesive layer, a primer layer which comprises a saturated polyester resin and is formed on the surface of the polyalkylene terephthalate film; and a second adhesive layer comprising a styrene-diene-styrene block copolymer containing a pharmaceutical agent layered on the primer layer. A method for the manufacture of the above-mentioned substrate sheet comprises preparing the above resin composition molding the resin composition into a composite film by a calendar process, and then adhering a polyalkylene terephthalate film on one side of the composite film by means of an adhesive layer thereby forming the substrate sheet, and forming a primer layer comprising a saturated polyester resin on the outer surface of the polyalkylene terephthalate film.

Another type of patch comprises incorporating the drug directly in a pharmaceutically acceptable adhesive and laminating the drug-containing adhesive onto a suitable backing member, e.g. a polyester backing membrane. The drug should be present at a concentration which will not affect the adhesive properties, and at the same time deliver the required clinical dose.

Transdermal patches may be passive or active. Passive transdermal drug delivery systems currently available, such as the nicotine, estrogen and nitroglycerine patches, deliver small-molecule drugs. Many of the other drugs are too large to be delivered through passive transdermal patches and may be delivered using technology such as electrical assist (iontophoresis) for large-molecule drugs.

Iontophoresis is a technique employed for enhancing the flux of ionized substances through membranes by application of electric current. One example of an iontophoretic membrane is given in U.S. Pat. No. 5,080,646 to Theeuwes. The principal mechanisms by which iontophoresis enhances molecular transport across the skin are (a) repelling a charged ion from an electrode of the same charge, (b) electroosmosis, the convective movement of solvent that occurs through a charged pore in response the preferential passage of counter-ions when an electric field is applied or (c) increase skin permeability due to application of electrical current.

Ocular formulations include, but are not limited to, liquid formulations (e.g., solutions, suspensions) for topical administration as well as formulation for injection or ocular insert administration. Preferably, the ocular formulation is formulated for topical administration such as an eye drop, swab, ointment, gel, or mist (for example, an aerosol or spray). In one embodiment, the formulation is an eye drop. For ocular formulations, the pharmaceutically acceptable excipients are selected to be compatible with, and suitable for, ocular use. Such excipients are well known in the art. In one embodiment, excipients may be selected to improve the solubility of the agent. Exemplary excipients include, but are not limited to, buffers, tonicity agents, viscosity agents, preservatives, emulsifiers, salts, lubricants, polymers, solvents, and other known excipients for ocular pharmaceutical formulations. Appropriate amounts can be determined by one of ordinary skill in the art, but non-limiting exemplary amounts (in % by weight) are also provided below.

In one embodiment, the pharmaceutical composition includes one or more buffers to adjust or maintain the pH of the formulation. In one embodiment, the pH is near physiological pH (pH of tears is about 7). Thus, the pH of the formulation can be about 6 to about 8, about 6.5 to about 7.5, about 6.8 to about 7.2, about 7.1 to about 7.5, or about 7. In another embodiment, the pH is about 5.5. Thus, the pH of the formulation can be about 4 to about 7, about 4.5 to about 6, about 4.5 to about 5.5, about 5.5 to about 6.5, about 5 to about 6, about 5.25 to about 5.75, or about 5.5. Exemplary buffers include, but are not limited to, phosphate buffers (e.g., sodium phosphate monobasic monohydrate, sodium phosphate dibasic anhydrous), borate buffers, and HBSS (Hank's Balanced Salt Solution). In one embodiment, the buffer is a phosphate buffer. In another embodiment, the buffer is sodium phosphate monobasic monohydrate and/or sodium phosphate dibasic anhydrous. The buffer amount (amount of either total buffer or a single buffer excipient) can be 0.1% to about 1.0%, about 0.2% to about 0.6%, about 0.05% to about 0.5%, about 0.25% to about 0.45%, or about 0.25%, about 0.43%, or about 0.7%. In one embodiment, the buffer is about 0.05% to about 0.5% (e.g., about 0.27%) sodium phosphate monobasic monohydrate and about 0.2% to about 0.6% (e.g., about 0.43%) sodium phosphate dibasic anhydrous.

In one embodiment, the pharmaceutical composition includes one or more tonicity agents. Although the formulation may be hypertonic or hypotonic, isotonic formulations are preferred (260-320 mOsm). Exemplary tonicity agents include, but are not limited to, sodium chloride. The tonicity agent amount can be about 0.1% to about 5%, about 0.1% to about 2%, about 0.1% to about 1%, about 0.25% to about 0.75%, about 0.2% to about 0.6%, or about 0.5%. In one embodiment, the tonicity agent is about 0.2% to about 0.6% (e.g., about 0.5%) sodium chloride.

In one embodiment the pharmaceutical composition includes one or more viscosity agents to increase the viscosity of the formulation. Exemplary viscosity agents include, but are not limited to, cellulosic agents (e.g., hydroxypropyl methylcellulose), polycarbophil, polyvinyl alcohol. In one embodiment, the viscosity agent is a cellulosic agent, e.g., hydroxypropyl methylcellulose. The viscosity agent amount can be about 0.1% to about 5%, about 0.1% to about 2%, about 0.1% to about 1%, about 0.1% to about 0.4%, or about 0.2%. In one embodiment, the viscosity agent is about 0.1% to about 0.4% (e.g., about 0.2%) hydroxypropyl methylcellulose.

In one embodiment, the pharmaceutical composition includes one or more preservatives to minimize microbial contamination or to enhance shelf life. Exemplary preservatives include, but are not limited to, benzalkonium chloride (BAK), cetrimonium, chlorobutanol, edetate disodium (EDTA), polyquaternium-1 (Polyquad®), polyhexamethylene biguanide (PHMB), stabilized oxychloro complex (PURITE®), sodium perborate, and SofZia®. The preservative amount may be, e.g., less than about 0.02%, about 0.004% or less, or about 0.005% to about 0.01%.

In one embodiment, the pharmaceutical composition includes one or more stabilizers. Exemplary stabilizers include, but are not limited to amino acids such as alanine. The stabilizer amount can be about 0.1% to about 5%, about 0.1% to about 2%, about 0.1% to about 1%, about 0.25% to about 0.75%, about 0.2% to about 0.6%, or about 0.5%. In one embodiment, the stabilizer is about 0.2% to about 0.6% (e.g., about 0.5%) alanine.

In one embodiment, the pharmaceutical composition includes one or more emulsifiers. Exemplary emulsifiers include, but are not limited to, Polysorbate 80.

The compounds described herein can be used in combination with one another, with other active agents known to be useful in ocular disease, or with adjunctive agents that may not be effective alone, but may contribute to the efficacy of the active agent. For example, adjunctive agents might include one or more amino acids or choline (separate from the lipoic acid compound) to enhance the efficacy of the active agent. The combinations can be advantageous, e.g., in reducing metabolic degradation.

The term "co-administer" means to administer more than one active agent, such that the duration of physiological effect of one active agent overlaps with the physiological effect of a second active agent. In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In one embodiment, one or more pharmaceutical excipients are selected from the group consisting of buffers, tonicity agents, and viscosity agents.

The pharmaceutical formulation may be packaged for administration by any means known in the art including, but not limited to, individual dose units or multi-dose units, e.g., dropper bottles. Multi-dose units may include, for example, about 1 mL to about 100 mL, about 1 mL to about 50 mL, about 1 mL to about 10 mL, about 2 mL to about 7 mL, or about 5 mL. An individual dose may be, e.g., 1-10 drops, 1-5 drops, or 2-3 drops, wherein each drop is about 5 to about 50 µl, about 10 to about 30 µl, or about 20 µl. Depending on the active agent concentration and the condition of the patient, doses may be administered.

EQUIVALENTS

The present disclosure provides among other things compositions and methods for treating neurological diseases and their complications. While specific embodiments of the subject disclosure have been discussed, the above specification is illustrative and not restrictive. Many variations of the systems and methods herein will become apparent to those skilled in the art upon review of this specification. The full scope of the claimed systems and methods should be determined by reference to the claims, along with their full scope of equivalents, and the specification, along with such variations.

INCORPORATION BY REFERENCE

All publications and patents mentioned herein, including those items listed above, are hereby incorporated by reference in their entirety as if each individual publication or patent was specifically and individually indicated to be incorporated by reference. In case of conflict, the present application, including any definitions herein, will control.

EXAMPLES

Synthesis of Compound of Formula I

Stage 1: Pilocarpine HCl in acetone was treated with sodium hydrogen carbonate for 18 h at room temperature to get free base of Pilocarpine which upon reaction with (R)-Lipoic acid at room temperature for 1 h gave Pilocarpine-(R)-Lipoate [5-(((3R,4S)-4-ethyl-5-oxotetrahydrofuran-3-yl)methyl)-1-methyl-1H-imidazol-1-ium (R)-5-(1,2-dithiolan-3-yl)pentanoate] in ~100% yield.

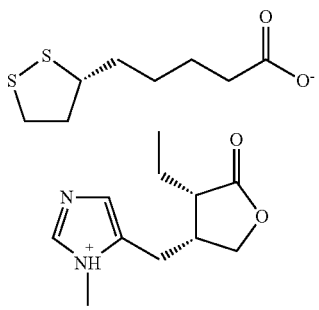

Stage 2: Stage 1 product was recrystallized from ethyl acetate (5 volumes) at 50-55° C. to afford yellow crystalline Pilocarpine-(R)-Lipoate n~80% yield.

Characterization of Pilocarpine-(R)-Lipoate By NMR

1H-NMR of Pilocarpine-(R)-Lipoate in DMSO-d6 solvent was obtained, and the chemical shift value for corresponding protons are provided in the Table 1 hereinbelow.

TABLE 1

Chemical shift value of 1H-NMR of Pilocarpine-(R)-Lipoate

| Position of the protons | Chemical shift (in δ ppm with multiplicity) |
|---|---|
| 27 Protons corresponding to aliphatic carbons | δ 0.99-1.02 (3H, t) |
| | δ 1.34-1.40 (2H, m) |
| | δ 1.47-1.57 (4H, m) |
| | δ 1.62-1.71 (2H, m) |
| | δ 1.84-1.90 (1H, m) |
| | δ 2.18-2.22 (2H, t) |
| | δ 2.31-2.43 (2H, m) |
| | δ 2.63-2.85 (3H, m) |
| | δ 3.08-3.21 (2H, m) |
| | δ 3.53 (3H, s) |
| | δ 3.59-3.63 (1H, m) |
| | δ 3.94-3.97 (1H, m) |
| | δ 4.18-4.22 (1H, m) |
| 2 Protons corresponding to aromatic carbons of the imidazole ring | δ 6.71 (1H, s) |
| | δ 7.51 (1H, s) |
| 1 Proton corresponding to quaternary NH$^+$ | δ 12.02 (1H, bs) |

Ocular Pharmacokinetic Study

A pharmacokinetics study was conducted on male New Zealand white rabbits to evaluate the ocular pharmacokinetics of CLX-156 (Pilocarpine-(R)-Lipoate) formulation. Animals were topically administered with 50 µL of CLX-156 in each eye, and the aqueous humour and blood samples were collected followed by sacrifice of the animals for collection of lens, cornea and iris region at a pre-determined time.

| Composition | Per microlitre |
|---|---|
| Pilocarpine-(R)-Lipoate | 29.4 mg* |
| Glycerin | 27 mg |
| L-Alanine | 5 mg |
| Water for Injection . . . qs | 1 mL |

*Approximate equivalent to 14.7 mg of R-lipoate

The aqueous humour and tissue concentration of Pilocarpine and (R)-Lipoic acid were measured at 0.5 h, 1 h, 2 h, 4 h and 8 h in 3 animals/time point/group (as provided in Table 2 and Table 3 hereinbelow). Further, (R)-Lipoic acid concentration was measured in the lens region, and Pilocarpine concentration was measured in iris region of each of the treated animals (as provided in Table 2 and Table 3). All the samples were analyzed using LCMS-MS by a fit for purpose method.

TABLE 2

Concentration of (R)-Lipoic acid in aqueous humour and lens region, observed during the pharmacokinetics study.

| Parameters | Concentration of (R)-Lipoic acid in aqueous humour | Concentration of (R)-Lipoic acid in lens region |
|---|---|---|
| $C_{max}$ | 21.067 (µg/mL) | 0.122 (µg/g) |
| $T_{max}$ | 0.50 (h) | 0.50 (h) |
| $AUC_{last}$ | 17.271 (µg*h/mL) | 0.364 (µg*h/g) |

TABLE 3

Concentration of Pilocarpine in aqueous humour and iris region, observed during the pharmacokinetics study.

| Parameters | Concentration of Pilocarpine in aqueous humour | Concentration of Pilocarpine in iris region |
|---|---|---|
| $C_{max}$ | 6.48 (µg/mL) | 1.962 (µg/g) |
| $T_{max}$ | 0.50 (h) | 0.50 (h) |
| $AUC_{last}$ | 6.359 (µg*h/mL) | 1.491 (µg*h/g) |

From the aforesaid study and results obtained therefrom, following observations were made—(a) maximum concentration of (R)-Lipoic acid, present in the aqueous humour and lens region was 21.067 µg/mL and 0.122 µg/g, respectively; (b) the (R)-Lipoic acid was detectable up to 2 to 4 h in the aqueous humor, however, sustained level of (R)-Lipoic acid was observed from 2 to 8 h in the lens region, in animals treated with CLX-156 formulation; (c) maximum concentration of pilocarpine present in the aqueous humour and iris region were found to be 6.48 µg/mL and 1.962 µg/g, respectively; (d) pilocarpine was detectable up to 4 h and 2 h in aqueous humour and iris region in animals treated with CLX-156 formulation.

The present disclosure provides compounds that provide better therapeutic benefit to patients and individuals suffering from eye disorders. The compound(s) of Formula I of the present disclosure aid(s) in reduction of elevated intraocular pressure (TOP) in patients with open-angle glaucoma or ocular hypertension, in management of acute angle-closure glaucoma, in prevention of postoperative elevated IOP associated with laser surgery, and induction of miosis, and improves lens elasticity and enhances accommodation of the eye in Presbyopics. The compound(s) of Formula I advantageously effects stabilization of lipoic acid and improves bioavailability thereof in ocular tissues. Accordingly, compositions of the present disclosure, including one or more compounds of Formula I, exhibits enhanced therapeutic activity and efficacy including superior safety and tolerability.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

I claim:

1. A compound of formula I:

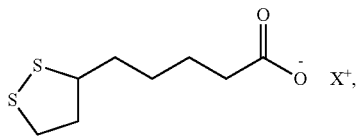

or a pharmaceutically acceptable hydrate, solvate, crystal, co-crystal, enantiomer, stereoisomer, polymorph or prodrug thereof, wherein X+ represents

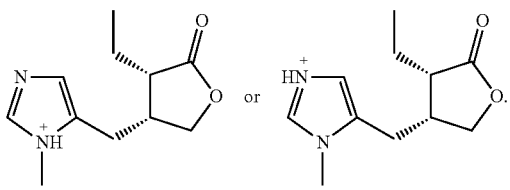

2. The compound of claim 1, wherein the compound is selected from the group consisting of

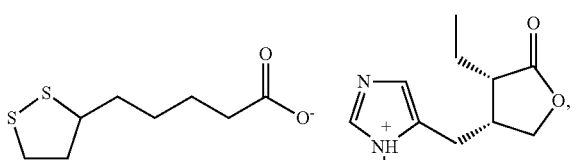

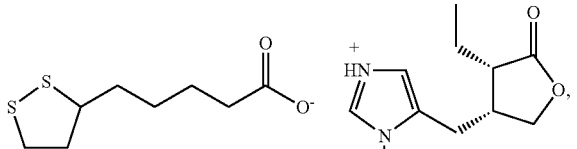

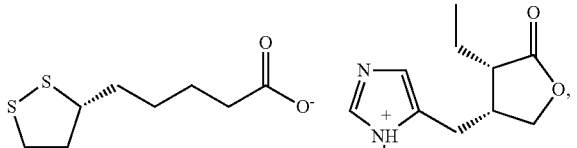

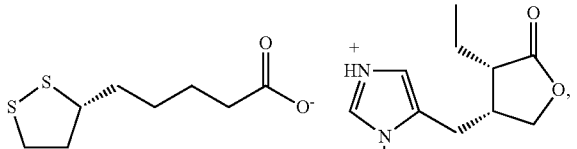

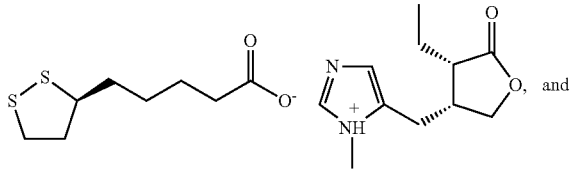

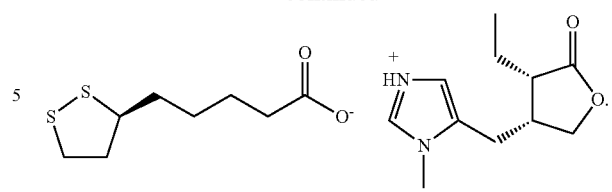

3. The compound of claim 1, for use in treating an eye disorder or complications thereof, wherein said eye disorder is selected from the group consisting of macular degeneration, cataract, glaucoma, diabetic retinopathy, dry eye, ocular neuritis, retinitis pigmentosa and presbyopia.

4. A pharmaceutical composition comprising at least one compound of claim 1 and a pharmaceutically acceptable excipient.

5. A pharmaceutical composition comprising at least one compound of claim 2 and a pharmaceutically acceptable excipient.

6. The pharmaceutical composition of claim 4, wherein said composition is formulated for oral, nasal, topical, rectal, vaginal, aerosol or parenteral administration.

7. The pharmaceutical composition of claim 5, wherein said composition is formulated for oral, nasal, topical, rectal, vaginal, aerosol or parenteral administration.

8. The pharmaceutical composition of claim 4, wherein said composition is selected from the group consisting of a topical ophthalmic formulation and ophthalmic drop formulation.

9. The pharmaceutical composition of claim 5, wherein said composition is selected from the group consisting of a topical ophthalmic formulation and ophthalmic drop formulation.

10. A method of synthesis of the compound of claim 1, the method comprising treating pilocarpine with lipoic acid.

11. A method of synthesis of the compound of claim 2, the method comprising treating pilocarpine with lipoic acid.

12. A medicament for treatment of an eye disorder or complications associated therewith comprising a compound of claim 1.

13. A medicament for treatment of an eye disorder or complications associated therewith, comprising a compound of claim 2.

14. A method of treating an eye disorder or complications thereof in a subject, wherein the method comprises administering to said subject a therapeutically effective amount of a compound of formula I Formula I

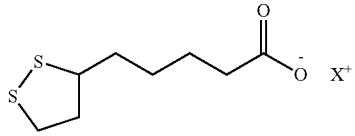

or a pharmaceutically acceptable hydrate, solvate, crystal, co-crystal, enantiomer, stereoisomer, polymorph or prodrug thereof, wherein X⁺ represents

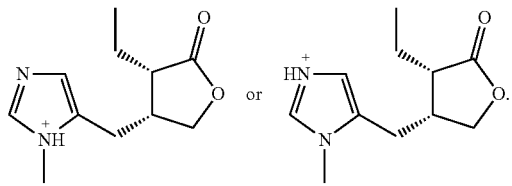 or

15. The method of claim 14, wherein said compound is selected from the group consisting of

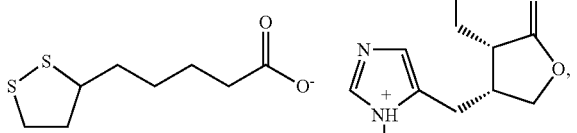

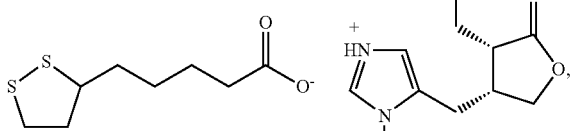

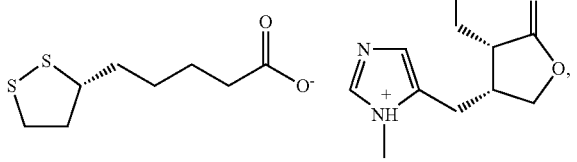

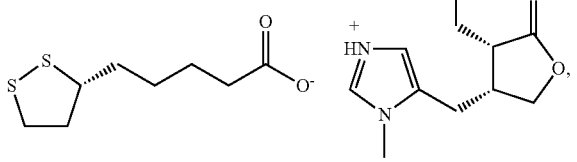

-continued

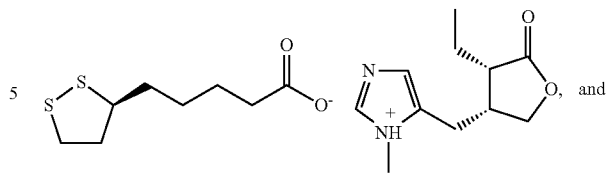

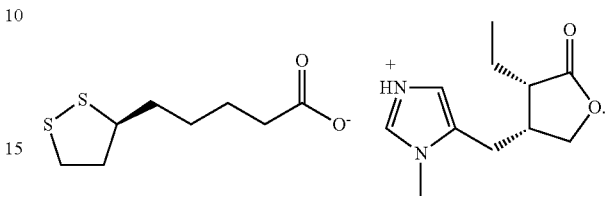

16. The method as claimed in claim 14, wherein said administering comprises oral, nasal, topical, rectal, vaginal, aerosol or parenteral administration of said compound.

17. The method as claimed in claim 14, wherein said compound is administered to said subject in combination with a pharmaceutically acceptable excipient.

18. The method as claimed in claim 14, wherein said compound is administered topically in a form of an eye drop, a swab, an ointment, a gel or a mist.

19. The method as claimed in claim 14, wherein said compound is administered topically to at least one eye of said subject.

20. The method as claimed in claim 14, wherein said therapeutically effective amount of said compound ranges from 0.001 mg to 1000 mg.

21. The method as claimed in claim 14, wherein said subject is a human.

22. The method as claimed in claim 14, wherein said eye disorder is selected from the group consisting of macular degeneration, cataract, glaucoma, diabetic retinopathy, dry eye, ocular neuritis, retinitis pigmentosa and presbyopia.

* * * * *

UNITED STATES PATENT AND TRADEMARK OFFICE
CERTIFICATE OF CORRECTION

| | |
|---|---|
| PATENT NO. | : 10,933,052 B2 |
| APPLICATION NO. | : 16/790492 |
| DATED | : March 2, 2021 |
| INVENTOR(S) | : Mahesh Kandula |

Page 1 of 1

It is certified that error appears in the above-identified patent and that said Letters Patent is hereby corrected as shown below:

In the Specification

Column 27, Line 56, "microlitre" should read --mL--.

Signed and Sealed this
Eleventh Day of October, 2022

Katherine Kelly Vidal
*Director of the United States Patent and Trademark Office*